United States Patent
Johansson et al.

(10) Patent No.: US 8,158,785 B2
(45) Date of Patent: Apr. 17, 2012

(54) 5,7-DISUBSTITUTED[1.3]THIAZOLO [4,5-D] PYRIMIDIN-2(3H)-AMINE DERIVATIVES AND THEIR USE IN THERAPY

(75) Inventors: Rolf Johansson, Sodertalje (SE); Sofia Karlstrom, Sodertalje (SE); Annika Kers, Sodertalje (SE); Gunnar Nordvall, Sodertalje (SE); Tobias Rein, Sodertalje (SE); Can Slivo, Sodertalje (SE)

(73) Assignee: AstraZeneca AB, Soderalje (SE)

( * ) Notice: Subject to any disclaimer, the term of this patent is extended or adjusted under 35 U.S.C. 154(b) by 337 days.

(21) Appl. No.: 12/442,831

(22) PCT Filed: Sep. 27, 2007

(86) PCT No.: PCT/SE2007/000858
§ 371 (c)(1),
(2), (4) Date: Mar. 25, 2009

(87) PCT Pub. No.: WO2008/039139
PCT Pub. Date: Apr. 3, 2008

(65) Prior Publication Data
US 2010/0035899 A1      Feb. 11, 2010

Related U.S. Application Data

(60) Provisional application No. 60/827,442, filed on Sep. 29, 2006, provisional application No. 60/828,122, filed on Oct. 4, 2006.

(51) Int. Cl.
| | |
|---|---|
| A61K 31/519 | (2006.01) |
| A61P 9/10 | (2006.01) |
| A61P 25/00 | (2006.01) |
| C07D 417/14 | (2006.01) |

(52) U.S. Cl. .................................. 544/255; 514/260.1
(58) Field of Classification Search ............... 514/260.1; 544/255
See application file for complete search history.

(56) References Cited

FOREIGN PATENT DOCUMENTS

| | | |
|---|---|---|
| WO | WO-0009511 A1 | 2/2000 |
| WO | WO-0158906 A1 | 8/2001 |
| WO | WO-0158907 A1 | 8/2001 |
| WO | WO-02076990 A1 | 10/2002 |
| WO | WO-2005033115 A1 | 4/2005 |
| WO | WO-2006064228 A2 | 6/2006 |
| WO | WO-2006107258 A1 | 10/2006 |

OTHER PUBLICATIONS

*Khimichesky Entsiklopedichesky Slovar*, Moscow, 1983, p. 130-131.

*Primary Examiner* — Sreeni Padmanabhan
*Assistant Examiner* — Sahar Javanmard

(57) ABSTRACT

There are disclosed novel 5-substituted 7-amino-[1,3]thiazolo[4,5-d]pyrimidine derivatives of formula (I) wherein $R^1$, $R^2$, $R^3$, $R^4$ and n are as defined in the specification, and pharmaceutically acceptable salts thereof, together with processes for their preparation, pharmaceutical compositions comprising them and their use in therapy. The compounds of formula (I) are $CX_3CR1$ receptor antagonists and are thereby particularly useful in the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

(I)

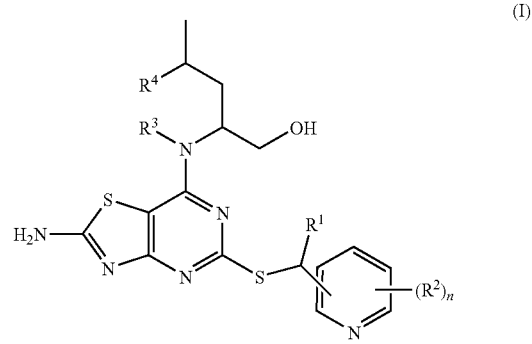

18 Claims, No Drawings

5,7-DISUBSTITUTED[1.3]THIAZOLO [4,5-D] PYRIMIDIN-2(3H)-AMINE DERIVATIVES AND THEIR USE IN THERAPY

CROSS-REFERENCE TO RELATED APPLICATIONS

This application is a U.S. National Stage under 35 U.S. §371 of International Application No. PCT/SE2007/000858 (filed 27 Sep. 2007) which claims priority under 35 U.S.C. §119(e)to Application No. 60/827,442 filed on 29 Sep. 2006, and Application No. 60/828,122 filed 4 Oct. 2006.

FIELD OF THE INVENTION

The present invention discloses novel 5-substituted 7-amino-[1,3]thiazolo[4,5-d]pyrimidine derivatives together with processes for their preparation, pharmaceutical formulations comprising them and their use in therapy.

BACKGROUND OF THE INVENTION

Chemokines play an important role in immune and inflammatory responses in various diseases and disorders, including asthma, atherosclerosis and allergic diseases, as well as autoimmune pathologies such as rheumatoid arthritis and multiple sclerosis. These small, secreted molecules are a growing superfamily of 8-14 kDa proteins characterised by a conserved cysteine motif. At the present time, the chemokine superfamily comprises four groups exhibiting characteristic structural motifs, the C—X—C, C—C and C—$X_3$—C and XC families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues. In contrast, members of the XC family lack one of the first two cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes, lymphocytes and neutrophils. Examples include human monocyte chemotactic proteins 1-3 (MCP-1, MCP-2 and MCP-3), RANTES (Regulated on Activation, Normal T-cell-Expressed and Secreted), eotaxin and the macrophage inflammatory proteins 1α and 1β (MIP-1α and MIP-1β).

The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family. These receptors represent good targets for drug development since agents that modulate these receptors would be useful in the treatment of disorders and diseases such as those mentioned above.

WO 01/58907 discloses certain 2-substituted 4-aminothiazolopyrimidine derivatives that are useful as antagonists of receptors linked to the C—X—C and C—C chemokine families, particularly as antagonists of the CXCR2 receptor.

The present invention relates to a group of compounds that are related to compounds disclosed in WO 01/58907 but are of a structural type not specifically exemplified therein. When compared to the Examples disclosed in WO 01/58907, the compounds of the present invention display surprisingly useful properties as antagonists of the $CX_3CR1$ receptor.

DISCLOSURE OF THE INVENTION

The present invention provides compounds of formula (I)

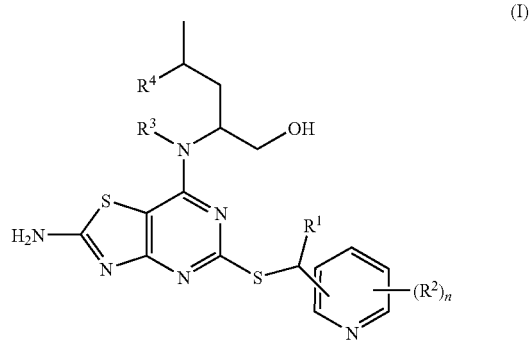

(I)

wherein:
$R^1$ represents $CH_3$ or $CF_3$;
$R^2$ represents halo, CN or $C_{1-6}$alkyl;
$R^3$ represents H or $CH_3$;
$R^4$ represents H or $CH_3$;
n represents 0, 1 or 2;
as a free base or a pharmaceutically acceptable salt, solvate or solvate of a salt thereof.

In one embodiment of the invention, there is provided compounds of formula (I), wherein n represents 1.

In another embodiment of the invention, there is provided compounds of formula (I), wherein $R^1$ represents $CH_3$.

In yet another embodiment of the invention, there is provided compounds of formula (I), wherein $R^2$ represents halo or CN.

In yet another embodiment of the invention, there is provided compounds of formula (I), wherein $R^2$ represents F or Cl.

In yet another embodiment of the invention, there is provided compounds of formula (I), wherein $R^2$ represents CN.

In yet another embodiment of the invention, there is provided compounds of formula (I), wherein n represents 1; $R^1$ represents $CH_3$; and $R^2$ represents F, Cl or CN.

In yet another embodiment of the invention, there is provided compounds of formula (I), wherein the pyridine is attached in its 5-position and has Cl in 2-position.

In yet another embodiment of the invention, there is provided compounds of formula (I), wherein the pyridine is attached in its 2-position and has CN in 4-position.

In yet another embodiment of the invention, there is provided compounds of formula (I), wherein the pyridine is attached in its 2-position and has F in 5-position.

In yet another embodiment of the invention, there is provided compounds of formula (I), wherein the pyridine is attached in its 2-position and has Cl in 5-position.

In yet another embodiment of the invention, there is provided compounds of formula (I), wherein the pyridine is attached in its 2-position and has F in 3-position.

In yet another embodiment of the invention, there is provided compounds of formula (I), wherein the pyridine is attached in its 4-position and has Cl in 3-position.

In yet another embodiment of the invention, there is provided compounds of formula (I), wherein $R^3$ represents H.

In yet another embodiment of the invention, there is provided compounds of formula (I), wherein $R^4$ represents $CH_3$.

In yet another embodiment of the invention, there is provided compounds of formula (I), selected from:
(2R)-2-[(2-amino-5-{[1-(5-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(5-chloropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(5-fluoropyridin-2-yl)ethyl]thio}[1,3]thiazolo[4,5-d]pyrimidin-7-yl)amino]-4-methylpentan-1-ol;
(2R)-2-[(2-amino-5-{[1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1R)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(6-chloropyridin-3-yl)ethyl]thio}[1,3]thiazolo[4,5-d]pyrimidin-7-yl)(methyl)amino]pentan-1-ol;
(2R)-2-[(2-amino-5-{[(1S)-1-(6-chloropyridin-3-yl)ethyl]thio}[1,3]thiazolo[4,5-d]pyrimidin-7-yl)amino]pentan-1-ol; and
2-{(1S)-1-[(2-amino-7-{[(1R)-1-(hydroxymethyl)-3-methylbutyl]amino}[1,3]thiazolo[4,5-d]pyrimidin-5-yl)thio]ethyl}isonicotinonitrile;
as a free base or a pharmaceutically acceptable salt, solvate or solvate of a salt thereof.

The compounds of formula (I) may exist in stereoisomeric and/or tautomeric forms. It is to be understood that all enantiomers, diastereomers, racemates, tautomers and mixtures thereof are included within the scope of the invention.

When compared to the compounds disclosed in WO 01/58907, the compounds of the present invention are characterised by the presence of the branched thioalkylpyridyl at the 5-position of the thiazolopyrimidine ring system. That is, the compounds of the present invention incorporate a $R^1$ group that is not hydrogen.

According to the invention, we further provide a process for the preparation of a compound of formula (I), or a pharmaceutically acceptable salt thereof which comprises:
a) reacting a compound of formula (II):

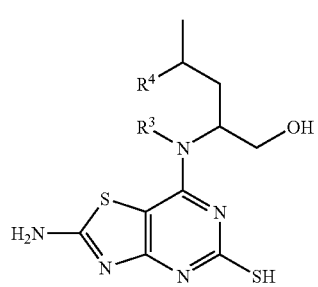

wherein $R^3$ and $R^4$ are as defined in formula (I);
with a compound of formula (III):

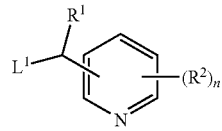

wherein $R^1$, $R^2$, and n are as defined in formula (I) and $L^1$ represents a leaving group; or
b) reacting a compound of formula (IV)

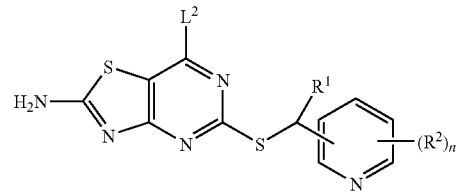

wherein $R^1$, $R^2$ and n are as defined in formula (I) and $L^2$ represents a leaving group;
with a compound of formula (V)

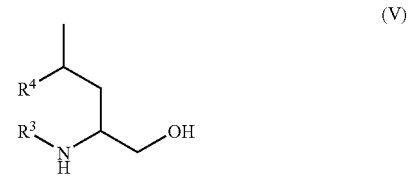

wherein $R^3$ and $R^4$ are as defined in formula (I);
and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), the reactants (II) and (III) are coupled together in a suitable organic solvent such as dimethylsulfoxide (DMSO), acetonitrile or 1-methyl-2-pyrrolidinone (NMP). The reaction is optionally performed in the presence of an added organic or inorganic base such as triethylamine, N,N-diisopropylethylamine (DIPEA) or sodium hydride. The reaction is optionally performed in the presence of a mild reducing agent such a sodium borohydride. The reaction is conducted at a suitable temperature, normally between room temperature and the boiling point of the solvent. The reaction is generally continued for a period of about one hour to one week, or until analysis indicates that formation of the required product is complete.

In process (b), the reactants (IV) and (V) are coupled together in a suitable organic solvent such as tetrahydrofuran, acetonitrile, dimethylsulphoxide or 1-methyl-2-pyrrolidinone. The reaction is optionally performed in the presence of an added base. This base may be an organic base such as triethylamine or N,N-diisopropylethylamine, or an inorganic base such as potassium carbonate. The reaction is conducted at a suitable temperature, normally between room temperature and the boiling point of the solvent, but optionally at higher temperatures if a sealed reaction vessel is used. The reaction is generally continued for a period of about one hour to one week, or until analysis indicates that formation of the required product is complete.

Suitable leaving groups $L^1$ and $L^2$ are halogen, particularly chloro or bromo. In one embodiment, $L^1$ and $L^2$ each represent chloro.

It will be apparent to a person skilled in the art that in the above processes it may be desirable or necessary to protect an amine, hydroxyl or other potentially reactive group. Suitable protecting groups and details of processes for adding and removing such groups are, in general, well known in the art. See, for example, "Protective Groups in Organic Synthesis", 3rd Edition (1999) by Greene and Wuts.

The present invention includes compounds of formula (I) in the form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question.

Salts of compounds of formula (I) may be formed by reacting the free compound, or a salt, enantiomer or racemate thereof, with one or more equivalents of the appropriate acid or base. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) are either known from for example WO 01/58907, WO01/25242, or WO 02/76990, or may be prepared using known methods that will be readily apparent to the man skilled in the art.

Compounds of formula (IV) may be prepared using methods analogous to those disclosed in for example WO 00/09511, or using other known methods that will be readily apparent to the man skilled in the art.

Compounds of formulae (III) and (V) are either commercially available, or known in the literature, or may be prepared using known methods that will be readily apparent to the man skilled in the art.

Suitable specific methods for the preparation of compounds of formulae (II), (III), (IV) and (V) are detailed in the Examples section of the present application and such methods represent specific embodiments of the processes of the invention.

For example, compounds of formula (II), and thence those of formula (I), may be prepared as shown in Scheme 1:

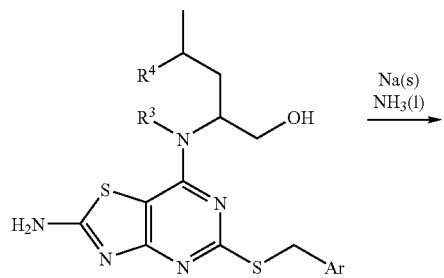

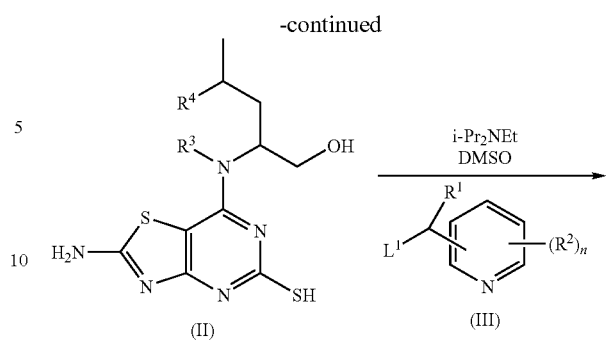

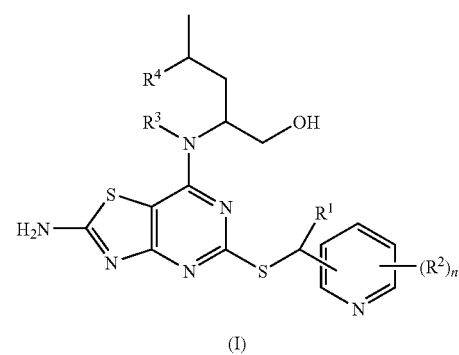

Intermediate compounds may be used as such or in protected form. Suitable protecting groups and details of processes for adding and removing such groups are, in general, well known in the art. See, for example, "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula (I) may exist in stereoisomeric forms. Therefore, all enantiomers, diastereomers, racemates and mixtures thereof are included within the scope of the invention. The various optical isomers may be isolated by separation of a stereoisomeric mixture of the compounds using conventional techniques, for example, fractional crystallisation, or HPLC. Alternatively, the various optical isomers may be prepared directly using optically active starting materials.

The compounds of formula (I) contain two stereogenic centres and may thus exist in four discrete stereoisomeric forms as shown in formulae (Ia) to (Id)

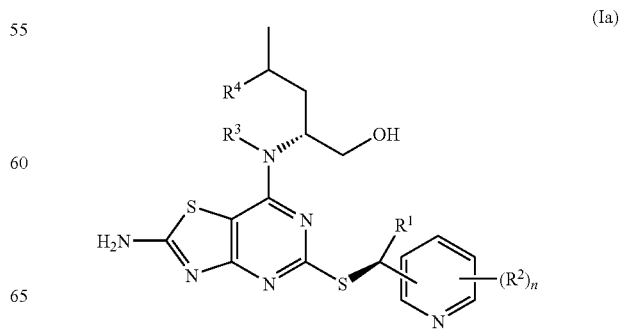

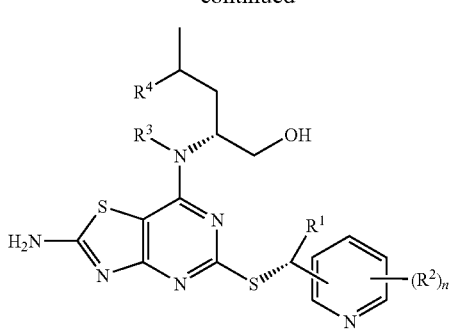
(Ib)

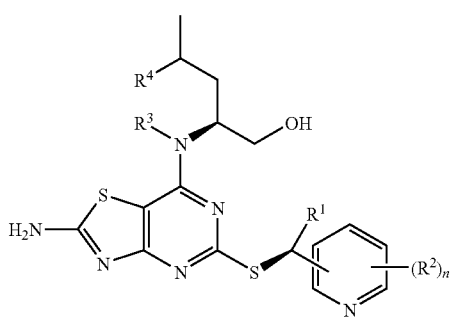
(Ic)

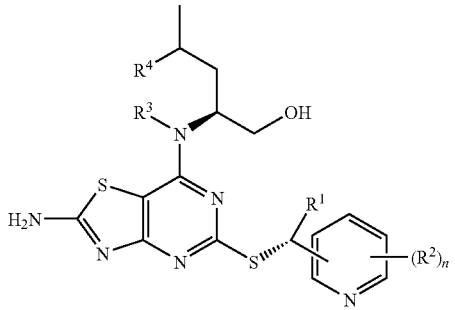
(Id)

All such four stereoisomers and any mixtures thereof are included within the scope of the invention. In one embodiment, the compounds of formula (I) have the stereochemistry shown in formula (Ia). In another embodiment, the compounds of formula (I) have the stereochemistry shown in formula (Ib).

Intermediate compounds may also exist in stereoisomeric forms and may be used as purified enantiomers, diastereomers, racemates or mixtures.

In this specification the term "$C_{1-6}$alkyl" includes both straight and branched chain as well as cyclic alkyl groups. $C_{1-6}$alkyl having 1 to 6 carbon atoms and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl, i-hexyl or cyclohexyl.

In this specification the term "halo" or "halogen" refers to fluoro, chloro, bromo, and iodo.

The compounds of formula (I), and their pharmaceutically acceptable salts are useful because they possess pharmacological activity as antagonists of the $CX_3CR1$ receptor. In particular, when compared to the compounds specifically exemplified in WO 01/58907, the compounds of formula (I) of the present invention possess significantly improved potencies for inhibition of the $CX_3CR1$ receptor and/or decreased potencies for inhibition of the CXCR2 receptor. Preferred compounds of the present invention display both enhanced potency for the inhibition of $CX_3CR1$ and decreased potency for inhibition of CXCR2.

In one aspect the present invention provides a compound of formula (I) or a pharmaceutically acceptable salt thereof, for use as a medicament.

In another aspect the present invention provides the use of a compound of formula (I) or a pharmaceutically acceptable salt thereof, in the manufacture of a medicament, for the treatment or prophylaxis of diseases or conditions in which antagonism of the $CX_3CR1$ receptor is beneficial.

In another aspect the present invention provides the use of a compound of formula (I) or a pharmaceutically acceptable salt thereof, in the manufacture of a medicament, for the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

In another aspect the present invention provides the use of a compound of formula (I) or a pharmaceutically acceptable salt thereof, in the manufacture of a medicament, for the treatment or prophylaxis of multiple sclerosis (MS).

In another aspect the present invention provides the use of a compound of formula (I) or a pharmaceutically acceptable salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

In another aspect the present invention provides the use of a compound of formula (I) or a pharmaceutically acceptable salt thereof, in the manufacture of a medicament, for the treatment or prophylaxis of atherosclerosis by changing the composition of the plaques to reduce the risk of plaque rupture and atherothrombotic events.

In another aspect the present invention provides the use of a compound of formula (I) or a pharmaceutically acceptable salt thereof, in the manufacture of a medicament, for the treatment or prophylaxis of stroke or transient brain injury (TBI).

According to the invention, there is also provided a method of treating, or reducing the risk of, diseases or conditions in which antagonism of the $CX_3CR1$ receptor is beneficial which comprises administering to a person suffering from or at risk of, said disease or condition, a therapeutically effective amount of a compound of formula (I) or a pharmaceutically acceptable salt thereof.

There is also provided a method of treating, or reducing the risk of, neurodegenerative disorders, demyelinating disease, cardio- and cerebrovascular atherosclerotic disorders, peripheral artery disease, rheumatoid arthritis, pulmonary diseases such as COPD, asthma or pain in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of, multiple sclerosis (MS) in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by preventing and/or reducing the formation of new atherosclerotic lesions or plaques and for by preventing or slowing progression of existing lesions and plaques in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of stroke or transient brain injury (TBI) in a person suffering from or at risk of, said disease or condition, wherein the method comprises administering to the person a therapeutically effective amount of a compound of formula (I) or a pharmaceutically acceptable salt thereof.

The compounds can be used as monotheraphy, or in combinations, either as prophylactic or therapeutic treatment of inflammatory conditions and diseases of the central nervous system such as stroke and transient brain injury (TBI). (Soriano et al. *J. Neuroimmunology* 2002, 125, 59-65.).

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of diseases or conditions in which antagonism of the $CX_3CR1$ receptor is beneficial.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of neurodegenerative disorders, demyelinating disease, cardio- and cerebrovascular atherosclerotic disorders, peripheral artery disease, rheumatoid arthritis, COPD, asthma or pain.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of multiple sclerosis.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

The compounds of formula (I) and their pharmaceutically acceptable salts are indicated for use in the treatment or prophylaxis of diseases or conditions in which modulation of activity at the $CX_3CR1$ receptor is desirable. In particular, the compounds are indicated for use in the treatment of neurodegenerative disorders or demyelinating disease in mammals including man. More particularly, the compounds are indicated for use in the treatment of multiple sclerosis. The compounds are also indicated to be useful in the treatment of pain, rheumatoid arthritis, osteoarthritis, cardio- and cerebrovascular atherosclerotic disorders, peripheral artery disease and pulmonary arterial hypertension.

Conditions that may be specifically mentioned are: neurodegenerative diseases and dementia disorders, for example, Alzheimer's disease, amyotrophic lateral sclerosis and other motor neuron diseases, Creutzfeldt-Jacob's disease and other prion diseases, HIV encephalopathy, Huntington's disease, frontotemporal dementia, Lewy body dementia and vascular dementia; polyneuropathies, for example, Guillain-Barré syndrome, chronic inflammatory demyelinating polyradiculoneuropathy, multifocal motor neuropathy and plexopathies; CNS demyelination, for example, acute disseminated/haemorrhagic encephalomyelitis and subacute sclerosing panencephalitis; neuromuscular disorders, for example, myasthenia gravis and Lambert-Eaton syndrome; spinal disorders, for example, tropical spastic paraparesis and stiff-man syndrome; paraneoplastic syndromes, for example, cerebellar degeneration and encephalomyelitis; traumatic brain injury; migraine; cancer; allograft rejection; systemic sclerosis; viral infections; parasite-transmitted diseases, for example, malaria; periodontal disease; myocardial infarction; stroke; coronary heart disease; ischaemic heart disease; restenosis; rheumatoid arthritis; pulmonary diseases such as COPD; asthma or pain.

The compounds of the invention are also indicated for use in the treatment of atherosclerosis by preventing and/or reducing the formation of new atherosclerotic lesions or plaques and/or by preventing or slowing progression of existing lesions and plaques.

The compounds of the invention are also indicated for use in the treatment of atherosclerosis by changing the composition of the plaques so as to reduce the risk of plaque rupture and atherothrombotic events.

The compounds of the invention are also indicated for use in the treatment of inflammatory bowel disease (IBD), for example, Crohn's disease and ulcerative colitis, by inducing remission and/or maintaining remission of IBD.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I) and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition that comprises mixing the ingredients.

The invention further relates to combination therapies wherein a compound of formula (I) or a pharmaceutically acceptable salt thereof, or a pharmaceutical composition or formulation comprising a compound of formula (I), is administered concurrently or sequentially with therapy and/or an agent for the treatment of any one of cardio- and cerebrovascular atherosclerotic disorders and peripheral artery disease.

In particular, a compound of formula (I) or a pharmaceutically acceptable salt thereof may be administered in association with compounds from one or more of the following groups:
1) anti-inflammatory agents, for example,
   a) NSAIDs (e.g. acetylsalicylic acid, ibuprofen, naproxen, flurbiprofen, diclofenac, indometacin);
   b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
   c) leukotriene receptor antagonists; (e.g. CP195543, amelubant, LY293111, accolate, MK571);
2) anti-hypertensive agents, for example,
   a) beta-blockers (e.g. metoprolol, atenolol, sotalol);
   b) angiotensin converting enzyme inhibitors (e.g. captopril, ramipril, quinapril, enalapril);
   c) calcium channel blockers (e.g. verapamil, diltiazem, felodipine, amlodipine);
   d) angiotensin II receptor antagonists (e.g. irbesartan, candesartan, telemisartan, losartan);
3) anti-coagulantia, for example,
   a) thrombin inhibitors (e.g. ximelagatran), heparines, factor Xa inhibitors;
   b) platelet aggregation inhibitors (e.g. clopidrogrel, ticlopidine, prasugel, AZ4160);
4) modulators of lipid metabolism, for example,
   a) insulin sensitizers such as PPAR agonists (e.g. pioglitazone, rosiglitazone, Galida, muraglitazaar, gefemrozil, fenofibrate);
   b) HMG-CoA reductase inhibitors, statins (e.g. simvastatin, pravastatin, atorvaststin, rosuvastatin, fluvastatin, pitavastatin);
   c) cholesterol absorption inhibitors (e.g. ezetimibe);
   d) IBAT inhibitors (e.g. AZD-7806);
   e) LXR agonists (e.g. GW-683965A, T-0901317);
   f) FXR receptor modulators;
   g) phospholipase inhibitors;
5) anti-anginal agents, for example, nitrates and nitrites;
6) modulators of oxidative stress, for example, anti-oxidants. (probucol), myeloperoxidase inhibitors.

The invention is illustrated, but in no way limited, by the following examples:

General Methods

All solvents used were analytical grade and commercially available anhydrous solvents were routinely used for reactions. Reactions were typically run under an inert atmosphere of nitrogen or argon.

$^1$H and $^{13}$C NMR spectra were recorded at 400 MHz for proton and 100 MHz for carbon-13 either on a Varian Unity+ 400 NMR Spectrometer equipped with a 5 mm BBO probe with Z-gradients, or a Bruker Avance 400 NMR spectrometer equipped with a 60 μl dual inverse flow probe with Z-gradients, or a Bruker DPX400 NMR spectrometer equipped with a 4-nucleus probe equipped with Z-gradients. 600 MHz $^1$H NMR spectra were recorded on a Bruker av600 NMR spectrometer equipped with a 5 mm BBI probehead with Z-gradients. 300 MHz $^1$H NMR spectra were recorded on a Varian Gemini 300 NMR equipped with a 5 mm BBI probehead. Unless specifically noted in the examples, spectra were recorded at 400 MHz for proton and 100 MHz for carbon-13. The following reference signals were used: the middle line of DMSO-$d_6$ δ 2.50 ($^1$H), δ 39.51 ($^{13}$C); the middle line of CD$_3$OD δ 3.31 ($^1$H) or δ 49.15 ($^{13}$C); acetone-$d_6$ 2.04 ($^1$H), 206.5 ($^{13}$C); and CDCl$_3$ δ 7.26 ($^1$H), the middle line of CDCl$_3$ δ 77.16 ($^{13}$C) (unless otherwise indicated).

Enantiomeric excess (ee) was determined by GC on a Cyclodex B column (isothermic elution 100° C.) or on a Cyclosil B column (temperature gradient 110-130° C.). Diastereomeric excess (de) was determined by HPLC.

Mass spectra were recorded on a Waters LCMS consisting of an Alliance 2795 (LC) and a ZQ single quadrupole mass spectrometer. The mass spectrometer was equipped with an electrospray ion source (ESI) operated in a positive or negative ion mode. The capillary voltage was 3 kV and the mass spectrometer was scanned from m/z 100-700 with a scan time of 0.3 or 0.8 s. Separations were performed on either Waters X-Terra MS, C8-columns, (3.5 μm, 50 or 100 mm×2.1 mm i.d.), or a ScantecLab's ACE 3 AQ column (100 mm×2.1 mm i.d.). The column temperature was set to 40° C. A linear gradient was applied using a neutral or acidic mobile phase system, running at 0% to 100% organic phase in 4-5 minutes, flow rate 0.3 ml/min. Neutral mobile phase system: acetonitrile/[10 mM NH$_4$OAc (aq.)/MeCN (95:5)], or [10 mM NH$_4$OAc (aq.)/MeCN (1/9)]/[10 mM NH$_4$OAc (aq.)/MeCN (9/1)]. Acidic mobile phase system: [133 mM HCOOH (aq.)/MeCN (5/95)]/[8 mM HCOOH (aq.)/MeCN (98/2)].

Alternatively, mass spectra were recorded on a GC-MS (GC 6890, 5973N MSD, Agilent Technologies) using a VF-5 MS column (ID 0.25 mm×30 m, 0.25 μm (Varian Inc.)). A linear temperature gradient was applied (40° C.-300° C.), 25° C./minute. The MS was equipped with a CI ion source and the reactant gas was methane. The MS was scanned between m/z 50-500 and the scan speed was set to 3.25 scan/s. HPLC analyses were performed on an Agilent HP1000 system consisting of G1379A Micro Vacuum Degasser, G1312A Binary Pump, G1367A Wellplate auto-sampler, G1316A Thermostatted Column Compartment and G1315B Diode Array Detector. Column: X-Terra MS, Waters, 4.6×50 mm, 3.5 μm. The column temperature was set to 40° C. and the flow rate to 1.5 ml/min. The Diode Array Detector was scanned from 210-300 nm, step and peak width were set to 2 nm and 0.05 min, respectively. A linear gradient was applied, run from 0% to 100% acetonitrile, in 4 min. Mobile phase: acetonitrile/10 mM ammonium acetate in 5% acetonitrile in MilliQ Water.

A typical workup procedure after a reaction consisted of extraction of the product with a solvent such as ethyl acetate, washing with water followed by drying of the organic phase over MgSO$_4$ or Na$_2$SO$_4$, and concentration of the solution in vacuo.

Thin layer chromatography (TLC) was performed on Merck TLC-plates (Silica gel 60 F$_{254}$) and UV was used to visualize the spots. Flash chromatography was preformed on a Combi Flash® Companion™ using RediSep™ normal-phase flash columns or on Merck Silica gel 60 (0.040-0.063 mm). Typical solvents used for flash chromatography were mixtures of chloroform/methanol, toluene/ethyl acetate and ethyl acetate/hexanes.

Preparative chromatography was run on a Gilson auto-preparative HPLC with a diode array detector using a XTerra MS column (C8, 19×300 mm, 7 μm), and a gradient with acetonitrile/0.1M ammonium acetate in 5% acetonitrile in MilliQ Water, ran from 20% to 60% acetonitrile, in 13 min, and a flow rate of 20 ml/min., unless stated otherwise in the examples. Alternatively, purification was achieved on a semi preparative Shimadzu LC-8A HPLC with a Shimadzu SPD-10A UV-vis.-detector equipped with a Waters Symmetry® column (C18, 5 μm, 100 mm×19 mm). Gradient with acetonitrile/0.1% trifluoroacetic acid in MilliQ Water, run from 35% to 60% acetonitrile in 20 min. Flow rate: 10 ml/min. Recrystallization was typically performed in solvents or solvent mixtures such as ether, ethyl acetate/heptanes and methanol/water.

The following abbreviations have been used: DCM=dichloromethane; de=diastereomeric excess; DIPCl=β-chlorodiisopinocamphenylborane (DIP-Chloride™); DIPEA=N,N-diisopropylethylamine; DMF=N,N-dimethylformamide; DMSO=dimethylsulfoxide; ee=enantiomeric excess; NCS=N-chlorosuccinimide; NMP=1-methyl-2-pyrrolidinone; THF=tetrahydrofuran; aq=aqueous; conc=concentrated.

Starting materials used were either available from commercial sources or prepared according to literature procedures and had experimental data in accordance to those reported. The following are examples of starting material that were prepared:
(2R)-2-[(2-amino-5-mercapto[1,3]thiazolo[4,5-d]pyrimidin-7-yl)amino]-4-methylpentan-1-ol: WO 02/076990 (Examples 1-5 and 8);
5-(benzylthio)-7-chloro[1,3]thiazolo[4,5-d]pyrimidin-2-amine: WO 00/09511 (Example 8);
5-fluoro-2-formylpyridine: WO 2005/066155 (Example 1);
5-Fluoro-pyridine-2-carbonitrile WO 2005/066155 (Example 3);
1-(3-Chloropyridin-4-yl)ethanone: Marsais, F. et al. *J. Organometal. Chem.* 1981, 216, 139-147 (Example 4);
2-acetyl-isonicotinonitrile: Citterio et al. *J. Chem. Res. Synopses* 1982, 10, 272-273 (Example 8); and
1-(6-Chloropyridin-3-yl)ethanone: Lee, C. et al. *J. Med. Chem.* 2001, 44, 2133 (Examples 6 and 7).

In the general methods that follow, Py represents an optionally substituted pyridyl.

General Method A

Sodium borohydride (0.1 equiv.), DIPEA (1.5 equiv.) and a compound of general formula (III) (1.2 equiv.) were added to a compound of general formula (II) (1.0 equiv.) in DMSO under a nitrogen atmosphere. The resulting reaction mixture was stirred at 40° C. until the reaction was complete (monitored by LC-MS, HPLC or TLC). The mixture was poured into ice water and the product was extracted with DCM or EtOAc. The combined organic phases were dried and concentrated in vacuo. The crude product was, if necessary, purified using preparative HPLC or by flash column chromatography.

General Method B1

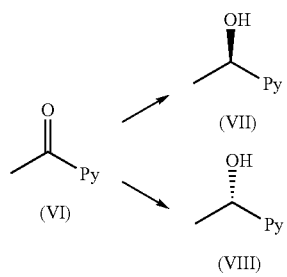

(VI) (1.0 equiv.) in THF was added at 0° C. to (+)-DIPCl (to give (VII)) or (−)-DIPCl (to give (VIII)) (1.5 equiv.) in THF under an argon atmosphere. The reaction mixture was allowed to slowly reach room temperature overnight. The solvent was evaporated off followed by the addition of $Et_2O$ and diethanolamine (2.2 equiv.). The mixture was stirred until the reaction was complete (monitored by LC-MS, HPLC or TLC). The precipitate that formed was filtered off, washed with $Et_2O$ and the filtrate was concentrated in vacuo. The crude product was, if necessary, purified using preparative HPLC or by flash column chromatography.

General Method B2

(R)-(+)-2-methyl-CBS-oxazaborolidine (1M in toluene, 0.1-1 equiv.) was dissolved in THF and cooled to 0° C. Borane-methyl sulfide complex (2M in THF, 1 equiv.) was added dropwise and the reaction mixture was stirred for 1 h. The reaction mixture was cooled to −10° C. and (VI) (1 equiv.), dissolved in THF was added dropwise over 0.5 h. The resulting mixture was stirred for 1 h, or until the reaction was complete, and the temperature was slowly raised to 10° C. 1M HCl aq. was added to quench the reaction. Saturated $NaHCO_3$ aq. was added until pH was approximately 8. The product was extracted with DCM. The combined organic extracts were dried over $Na_2SO_4$ and concentrated in vacuo to yield (VIII). The product was optionally purified by column chromatography.

General Method C1

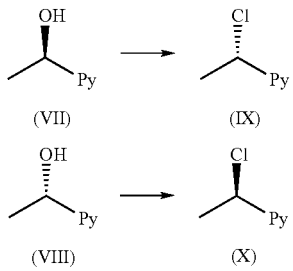

Triphenyl phosphine (1.3 equiv.) in THF was added at 0° C. to NCS (1.3 equiv.) in THF under an argon atmosphere. The resulting mixture was stirred at ambient temperature for 30 min. (VII) or (VIII) (1 equiv.) was added at 0° C. and the reaction mixture was stirred at ambient temperature until the reaction was complete (monitored by LC-MS, HPLC or TLC). The solvent was evaporated off followed by addition of hexane and removal of the precipitate by filtration. The filtrate was concentrated in vacuo to yield (IX) or (X). The crude product was, if necessary, purified using preparative HPLC or by flash column chromatography.

General Method C2

Cyanuric chloride (0.6 equiv.) was dissolved in ethyl acetate. DMF (1.5 equiv.) was added and the mixture was stirred at room temperature for 10 min. The reaction mixture was cooled to 0° C. (VII) or (VIII) (1 equiv.) was dissolved in ethyl acetate and added dropwise during 10 min. The resulting mixture was stirred at room temperature over night. Isopropanol (ca 0.25 mL/mmol (VII) or (VIII)) was added. The precipitate was filtered off and washed with EtOAc. The filtrate was concentrated to yield the title compound (IX) or (X).

EXAMPLE 1

(2R)-2-[(2-Amino-5-{[1-(5-fluoropyridin-2-yl)ethyl]thio}1,3]thiazolo[4,5-d]pyrimidin-7-yl)amino]-4-methylpentan-1-ol

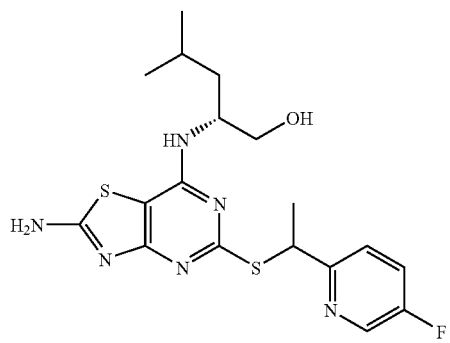

a) 1-(5-Fluoropyridin-2-yl)ethanol

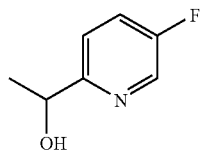

To a −78° C. solution of 5-fluoro-2-formylpyridine (0.66 g, 5.3 mmol) in THF (20 mL) was methyl lithium (1.6 M in diethyl ether, 4.0 mL) added dropwise. After stirring for 1.5 h at −78° C. a saturated solution of ammonium chloride (25 mL) followed by water (25 mL) was added. The mixture was extracted with chloroform and the organic phase was dried over magnesium sulphate and concentrated in vacuo. The residue was purified by flash column chromatography (eluent: chloroform:methanol 98:2) affording the title compound (0.25 g, 33% yield).

$^1$H NMR (400 MHz, CDCl$_3$): δ ppm 8.38 (d, 1 H), 7.42 (dt, 1 H), 7.33 (dd, 1 H), 4.90 (q, 1 H), 3.90 (s, 1 H), 1.50 (d, 3 H); MS (ESI) m/z 142 [M+1]$^+$.

b) 2-(1-Chloroethyl)-5-fluoropyridine

A mixture of triphenylphospine (0.92 g, 3.5 mmol) and CCl$_4$ (4 mL) was stirred for 10 min. and then a solution of 1-(5-fluoropyridin-2-yl)ethanol (0.25 g, 1.7 mmol) in DCM (2 mL) was added. After 18 h, pentane (20 mL) was added, the solid material was removed by filtration and the filtrate was concentrated in vacuo. The residue was purified by flash column chromatography (eluent heptane:ethyl acetate 3:1) affording the title compound (8 mg, 3% yield).

$^1$H NMR (400 MHz, CDCl$_3$): δ ppm 8.35 (d, 1 H), 7.44 (dd, 1 H), 7.36 (dt, 1 H), 5.09 (q, 1H), 1.81 (d, 3 H).

c) (2R)-2-[(2-Amino-5-{[1-(5-fluoropyridin-2-yl)ethyl]thio}[1,3]thiazolo[4,5-d]pyrimidin-7-yl)amino]-4-methylpentan-1-ol

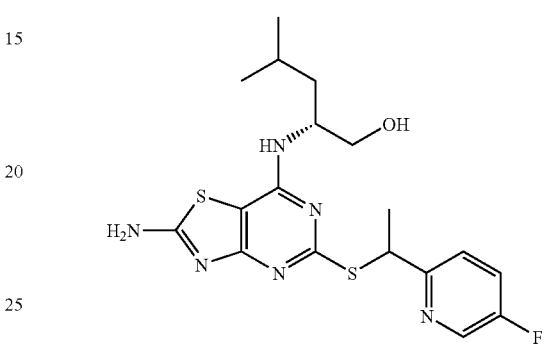

The title compound was prepared according to General method A starting from (2R)-2-[(2-amino-5-mercapto[1,3]thiazolo[4,5-d]pyrimidin-7-yl)amino]-4-methylpentan-1-ol (21 mg, 0.072 mmol) and 2-(1-chloroethyl)-5-fluoropyridine (8 mg, 0.048 mmol). Purification by preparative HPLC yielded 4 mg (21% yield) of the title compound as a mixture of diastereomers.

$^1$H NMR (400 MHz, DMSO-d$_6$): δ ppm 8.44 (t, 1H), 7.91 (s, 2H), 7.55-7.64 (m, 1H), 7.47-7.55 (m, 1H), 6.83 (d, 1H), 4.99-5.11 (m, 1H), 4.59 (q, 1H), 3.41-3.28 (m, 2H), 1.60 (dd, 3H), 1.48-1.57 (m, 1H), 1.25-1.42 (m, 2H), 0.72-0.86 (m, 6H); MS (ESI) m/z 423 [M+1]$^+$.

EXAMPLE 2

(2R)-2-[(2-Amino-5-{[(1S)-1-(5-chloropyridin-2-yl)ethyl]thio}[1,3]thiazolo[4,5-d]pyrimidin-7-yl)amino]-4-methylpentan-1-ol

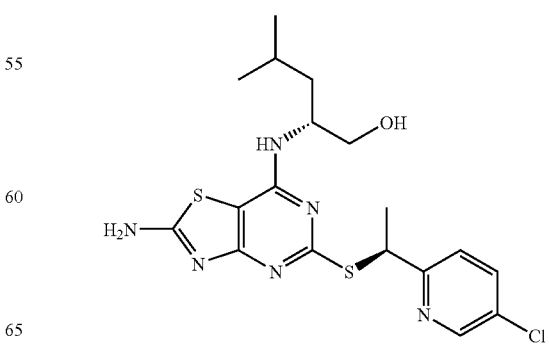

a) 1-(5-Chloropyridin-2-yl)ethanone

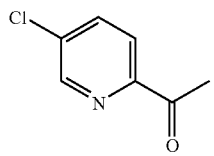

5-Chloropyridine-2-carbonitrile (10.7 g, 77 mmol) was dissolved in diethyl ether (65 mL) and THF (35 mL) under a nitrogen atmosphere. The mixture was cooled until the internal temperature was −63° C. Methylmagnesium bromide (3M in THF, 35 mL, 105 mmol) was added over 30 min. The reaction mixture was then left stirring at −60° C. for 45 min and was then warmed to room temperature. THF (50 mL) was added to dissolve any precipitated material and the reaction mixture was stirred for 1 h. 2M HCl aq. (100 mL) was added and the reaction mixture was stirred for 4 h. The pH was then adjusted to 7 with sodium bicarbonate. The phases were separated and the product extracted from the aqueous phase with DCM. The combined organic extracts were dried over sodium sulphate and concentrated in vacuo. The product was purified by flash column chromatography (eluent heptane:EtoAc gradient) to yield 7.9 g (64% yield) of the title compound.

$^1$H NMR (300 MHz, CDCl$_3$) δ ppm 8.62 (m, 1H); 8.00 (m, 1H); 7.80 (m, 1H); 2.70 (s, 3H).

b) (1S)-]-(5-Chloropyridin-2-yl)ethanol

The title compound was prepared by General method B2 starting from 1-(5-chloropyridin-2-yl)ethanone (780 mg, 5 mmol). Purification by flash column chromatography yielded 695 mg (88% yield) of the title compound with 92% ee.

$^1$H NMR (300 MHz, CDCl$_3$): 8.47 (s, 1H); 7.65 (d, 1H); 7.26 (d, 1H); 4.87 (q, 1H); 3.87 (br s, 1H); 1.47 (d, 3H); MS (ESI) m/z 140 and 142 [M+1]$^+$.

c) 5-Chloro-2-[(1R)-1-chloroethyl]pyridine

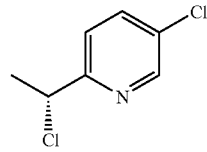

The title compound was prepared by General method C2 starting from (1S)-1-(5-chloropyridin-2-yl)ethanol (695 mg, 4.41 mmol). The crude product was used in the next step without purification.

$^1$H NMR (400 MHz, CDCl$_3$): δ ppm 8.46 (d, 1 H), 7.64 (dd, 1 H), 7.41 (d, 1 H), 5.08 (q, 1 H), 1.80 (d, 3 H); MS (ESI) m/z 176 and 178 [M+1]$^+$.

d) (2R)-2-[(2-Amino-5-{[(1S)-1-(5-chloropyridin-2-yl)ethyl]thio}[1,3]thiazolo[4,5-d]pyrimidin-7-yl)amino]-4-methylpentan-1-ol

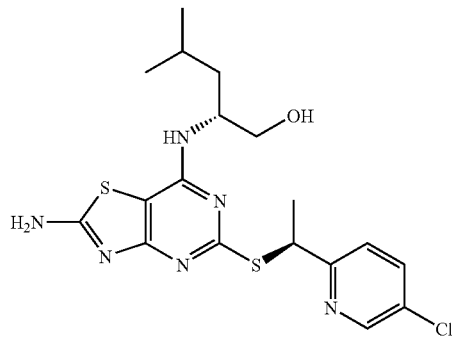

The title compound was prepared by general method A starting from (2R)-2-[(2-amino-5-mercapto[1,3]thiazolo[4,5-d]pyrimidin-7-yl)amino]-4-methylpentan-1-ol (572 mg, 1.91 mmol) and 5-chloro-2-[(1R)-1-chloroethyl]pyridine (376 mg, 2.1 mmol). Purification by preparative HPLC yielded 99 mg (12% yield) of the title compound.

$^1$H NMR (400 MHz, CD$_3$OD): δ ppm 8.49 (d, 1H), 7.79 (dd, 1H), 7.66 (d, 1H), 5.22 (q, 1H), 4.46 (br s, 1H), 3.57-3.40 (m, 2H), 1.78-1.66 (m, 4H), 1.61-1.40 (m, 2H), 1.03-0.93 (m, 6H); MS (ESI) m/z 439 and 441 [M+1]$^+$.

EXAMPLE 3

(2R)-2-[(2-Amino-5-{[(1S)-1-(5-fluoropyridin-2-yl)ethyl]thio}1,3]thiazolo[4,5-d]pyrimidin-7-yl)amino]-4-methylpentan-1-ol

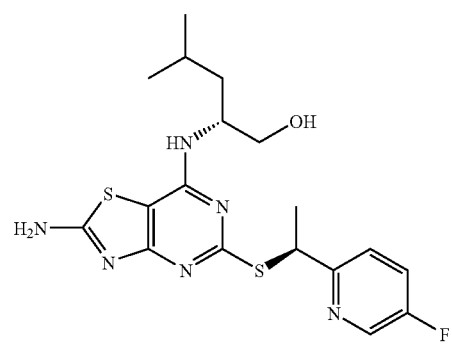

a) 1-(5-Fluoropyridin-2-yl)ethanone

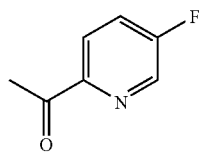

5-Fluoro-pyridine-2-carbonitrile (29 g, 240 mmol) was dissolved in THF (150 mL) under a nitrogen atmosphere. The reaction mixture was cooled to an internal temperature of −64° C. Methyl magnesium bromide (3M in THF, 105 mL, 315 mmol) was added over 40 min. The reaction mixture was stirred at −65° C. for 1.5 h, then warmed to room temperature. THF (50 mL) was added and the mixture was stirred an additional 3 h. 2M hydrochloric acid (aq., 100 mL) was added until the mixture was slightly acidic and the reaction mixture was stirred at room temperature overnight. Sodium bicarbonate was then added to neutralize the reaction mixture. The phases were separated and the aqueous phase was extracted with DCM. The combined organic extracts were washed with Brine, dried over sodium sulphate and concentrated in vacuo. The crude product was purified by flash column chromatography to yield 18 g (55% yield) of the title compound.

1H NMR (300 MHz, CDCl$_3$): 8.50 (m, 1H); 8.10 (m, 1H); 7.52 (m, 1H); 2.70 (s, 3H).

b) (1S)-1-(5-Fluoropyridin-2-yl)ethanol

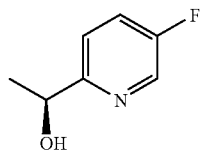

The title compound was prepared by General method B2 starting from 1-(5-fluoropyridin-2-yl)ethanone (2.70 g, 19.4 mmol). Purification by flash column chromatography yielded 0.85 g (31% yield) of the title compound with 94% ee.

$^1$H NMR (300 MHz, CDCl$_3$): 8.38 (m, 1H); 7.5-7.2 (m, 2H); 4.89 (q, 1H); 3.9 (br s, 1H); 1.49 (d, 3H).

c) 2-[(1R)-1-Chloroethyl]-5-fluoropyridine

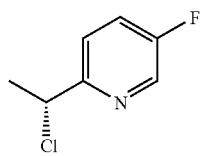

The title compound with 87% ee was prepared by General method C2 starting from (1S)-1-(5-fluoropyridin-2-yl)ethanol (407 mg, 2.9 mmol). The crude product was used in the next step without purification.

$^1$H NMR (300 MHz, CDCl$_3$): 8.44-8.40 (m, 1H); 7.6-7.4 (m, 2H); 5.16 (q, 1H); 1.86 (d, 3H).

d) (2R)-2-[(2-Amino-5-{[(1S)-1-(5-fluoropyridin-2-yl)ethyl]thio}[1,3]thiazolo[4,5-d]pyrimidin-7-yl)amino]-4-methylpentan-1-ol

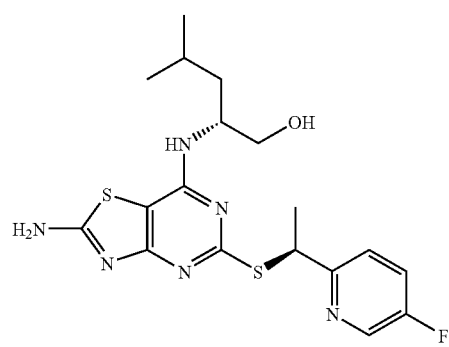

The title compound was prepared by General method A starting from (2R)-2-[(2-amino-5-mercapto[1,3]thiazolo[4,5-d]pyrimidin-7-yl)amino]-4-methylpentan-1-ol (550 mg, 1.8 mmol) and 2-[(1R)-1-chloroethyl]-5-fluoropyridine (0.46 g, 2.9 mmol). The product was purified by flash column chromatography followed by preparative HPLC (Column: Reprosil, eluent isopropanol:heptane 20:80, flow: 16 mL/min) collecting the first eluting isomer, to yield 135 mg (18% yield) of the title compound.

$^1$H NMR (400 MHz, DMSO-d$_6$) δ ppm 8.51 (d, 1H), 7.98 (s, 2H), 7.65 (dt, 1H); 7.58 (dd, 1H), 6.88 (d, 1H); 5.12 (q, 1H); 4.66 (t, 1H); 4.27 (br s, 1H); 3.41-3.27 (m, 2H), 1.66 (d, 3H), 1.65-1.55 (m, 1H); 1.48-1.35 (m, 2H), 0.88 (d, 3H), 0.85 (d, 3H); MS (ESI) m/z 423 [M+1]$^+$.

EXAMPLE 4

(2R)-2-[(2-amino-5-{[1-(3-chloropyridin-4-yl)ethyl]thio}[1,3]thiazolo[4,5-d]pyrimidin-7-yl)amino]-4-methylpentan-1-ol

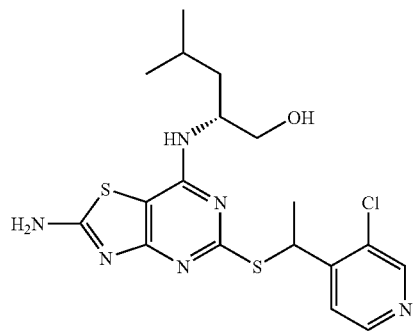

a) (1S)-1-(3-Chloropyridin-4-yl)ethanol

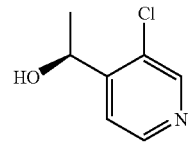

The title compound with 90% ee was prepared using General method B1 starting from 1-(3-chloropyridin-4-yl)ethanone (0.90 g, 5.78 mmol).

$^1$H NMR (300 MHz, CDCl$_3$) 8.47 (s, 1H); 7.65 (d, 1H); 7.26 (d, 1H); 4.87 (q, 1H); 3.87 (br s, 1H); 1.47 (d, 3H); MS (ESI) m/z 158 and 160 [M+1]$^+$.

b) 3-Chloro-4-[(1R)-1-chloroethyl]pyridine

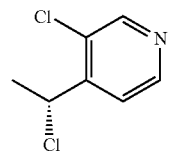

The title compound was prepared using General method C2 starting from (1S)-1-(3-chloropyridin-4-yl)ethanol (570 mg, 3.62 mmol). The crude product was used in the next step without purification.

MS (ESI) m/z 176 and 178 [M+1]⁺.

c) (2R)-2-[(2-Amino-5-{[1-(3-chloropyridin-4-yl)ethyl]thio}[1,3]thiazolo[4,5-d]pyrimidin-7-yl)amino]-4-methylpentan-1-ol (isomer 1 and isomer 2)

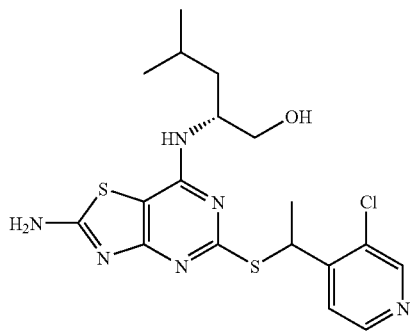

The title compound was prepared using General method A starting from (2R)-2-[(2-amino-5-mercapto[1,3]thiazolo[4,5-d]pyrimidin-7-yl)amino]-4-methylpentan-1-ol (860 mg, 2.87 mmol) and 3-chloro-4-[(1R)-1-chloroethyl]pyridine from the previous step. Purification by flash chromatography yielded the title compound (105 mg, 8% yield) as a diastereomeric mixture.

MS (ESI) m/z 439 and 441 [M+1]⁺.

EXAMPLE 5

(2R)-2-[(2-Amino-5-{[(1S)-1-(3-fluoropyridin-2-yl)ethyl]thio}[1,3]thiazolo[4,5-d]pyrimidin-7-yl)amino]-4-methylpentan-1-ol

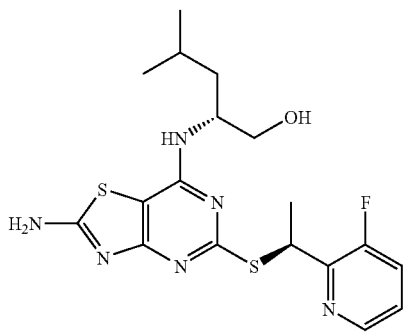

a) 1-(6-Bromo-3-fluoro-pyridin-2-yl)ethanone

2-Bromo-5-fluoro-pyridine (11 g, 62.5 mmol) was dissolved in diethyl ether at room temperature under a nitrogen atmosphere. The reaction mixture was cooled until the internal temperature was −66° C. Butyl lithium (2.5 M in hexanes, 26 mL, 65 mmol) was added dropwise over 0.5 h. The resulting reaction mixture was left at −65° C. for 1 h. N,N-Dimethylacetamide (6.5 mL, 70 mmol) was added over 10 min. and the reaction mixture was stirred at −65° C. for 2 h. 1M hydrochloric acid aq. (50 mL) was added and the mixture was warmed to room temperature. The pH was adjusted to 7 with additional hydrochloric acid. The aqueous phase was extracted with diethyl ether three times. The combined organic phases were washed with Brine, dried over sodium sulphate, and concentrated in vacuo. Purification by flash column chromatography (eluent heptane:diethyl ether gradient) yielded 4.6 g (34% yield) of the title compound.

¹H NMR (300 MHz, DMSO-d₆): 8.0-7.8 (m, 2H); 2.57 (s, 3H); MS (ESI) m/z 218 and 220 [M+1]⁺.

b) (1S)-1-(6-Bromo-3-fluoro-pyridin-2-yl)ethanol

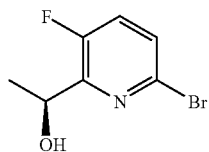

The title compound was prepared using General method B2 starting from 1-(6-bromo-3-fluoro-pyridin-2-yl)ethanone (1.76 g, 8.19 mmol). The product was purified by flash column chromatography (eluent: heptane:ethyl acetate gradient) to yield 1.31 g (73% yield) of the title compound with 80% ee.

¹H NMR (300 MHz, CDCl₃) 7.38 (m, 1H); 7.26 (m, 1H); 5.06 (q, 1H); 3.38 (br s, 1H); 1.47 (d, 3H); MS (ESI) m/z 220 and 222 [M+1]⁺, m/z 202 [M−H₂O]⁺.

c) (1S)-1-(3-Fluoro-pyridin-2-yl)ethanol

(1S)-1-(6-Bromo-3-fluoro-pyridin-2-yl)ethanol (1.3 g, 5.9 mmol), triethylamine (1.6 mL, 11.5 mmol) and palladium on carbon (0.64 g, 0.34 mmol) were mixed in DCM (25 mL). The flask was evacuated/filled with hydrogen gas in 4 cycles and then left at 2.5 atm pressure hydrogen gas at room temperature for 24 h. The mixture was filtered and the solid washed with DCM. The filtrate was washed with water and Brine and dried over sodium sulphate and concentrated in vacuo. The crude product was purified by flash column chromatography (eluent DCM:methanol gradient) to yield 0.54 g (65% yield) of the title compound.

¹H NMR (300 MHz, CDCl₃): 8.38 (m, 1H); 7.39 (m, 1H); 7.26 (m, 1H); 5.11 (q, 1H); 4.16 (br s, 1H); 1.49 (d, 3H).

d) 2-((R)-1-Chloroethyl)-3-fluoro-pyridine

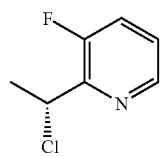

The title compound (0.24 g) was prepared using General method C2 starting from (1S)-1-(3-fluoro-pyridin-2-yl)ethanol (254 mg, 1.8 mmol).

$^1$H NMR (300 MHz, CDCl$_3$): 8.46 (m, 1H); 7.47 (m, 1H); 7.34 (m, 1H); 5.48 (q, 1H); 1.94 (d, 3H); MS (ESI) m/z 160 and 162 [M+1]$^+$.

e) (2R)-2-[(2-Amino-5-{[(1S)-1-(3-fluoropyridin-2-yl)ethyl]thio}[1,3]thiazolo[4,5-d]pyrimidin-7-yl)amino]-4-methylpentan-1-ol

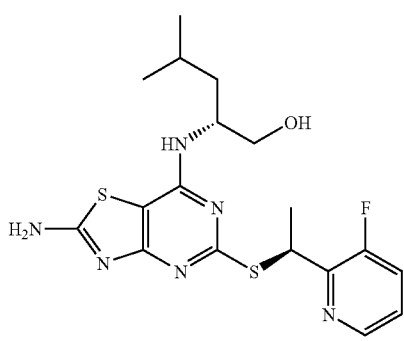

The title compound was prepared using General method A starting from (2R)-2-[(2-amino-5-mercapto[1,3]thiazolo[4,5-d]pyrimidin-7-yl)amino]-4-methylpentan-1-ol (348 mg, 1.16 mmol) and 2-((R)-1-chloroethyl)-3-fluoro-pyridine (240 mg, 1.5 mmol). Purification by flash column chromatography (eluent DCM:methanol gradient) resulted in 190 mg (47% yield) of the title compound with a diastereomeric excess of 60%. Of this material 55 mg was further purified by preparative HPLC. The last eluting isomer was collected to yield 21 mg of the title compound.

$^1$H NMR (400 MHz, DMSO-d$_6$) δ ppm 8.40 (dt, 1H), 7.98 (s, 2H), 7.70 (m, 1H), 7.40 (m, 1H); 6.92 (d, 1H); 5.45 (q, 1H); 4.65 (t, 1H); 4.27 (br s, 1H); 3.45-3.30 (m, 2H), 1.69 (d, 3H), 1.66-1.58 (m, 1H), 1.50-1.35 (m, 2H), 0.88 (d, 3H), 0.85 (d, 3H); MS (ESI) m/z 423 [M+1]$^+$.

EXAMPLE 6

(2R)-2-[(2-Amino-5-{[(1S)-1-(6- chloropyridin-3-yl)ethyl]thio}[1,3]thiazolo}4,5-d]pyrimidin-7-yl)(methyl)amino]pentan-1-ol

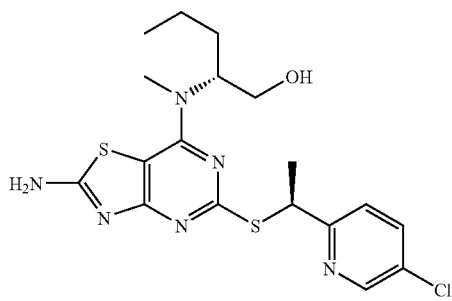

a) (1S)-1-(6-Chloropyridin-3-yl)ethanol

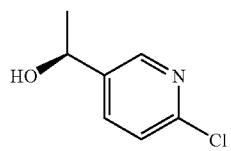

The title compound was prepared in accordance with the General method B1 using (−)DIPCl and 1-(6-chloropyridin-3-yl)ethanone (0.80 g, 5.14 mmol), affording 0.71 g (88% yield) of the title compound.

$^1$H NMR (CDCl$_3$) δ ppm 8.40-8.28 (m, 1H), 7.75-7.63 (m, 1H), 7.35-7.24 (m, 1H), 5.04-4.79 (m, 1H), 1.63-1.45 (m, 3H); MS (ESI) m/z 158 and 160 [M+1]$^+$.

b) 2-Chloro-5-[(1R)-1-chloroethyl]pyridine

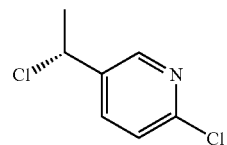

The title compound was prepared in accordance with the general method C1 using (1S)-1-(6-chloropyridin-3-yl)ethanol (0.20 g, 1.27 mmol), affording 0.16 g (72% yield) of the title compound.

$^1$H NMR (CDCl$_3$) δ ppm 8.45-8.35 (m, 1H), 7.79-7.70 (m, 1H), 7.39-7.29 (m, 1H), 5.07 (q, 1H), 1.85-1.78 (m, 3H); MS (ESI) m/z 176 and 178 [M+1]$^+$.

c) N-(Ethoxycarbonyl)-D-norvaline

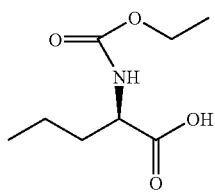

D-Norvaline (10.0 g, 85.3 mmol) was dissolved in aqueous sodium hydroxide (4M, 25 mL). Ethyl chloroformate (10.6 mL, 111 mmol) and aqueous sodium hydroxide (4M, 25 mL) was added over 15 min. at 0° C. The reaction mixture was warmed to room temperature and stirred at this temperature for 4 h. The reaction mixture was washed with diethyl ether three times and then acidified with aqueous hydrochloric acid (2M). The product was extracted with diethyl ether three times. The combined organic phases were dried over magnesium sulphate and concentrated in vacuo to yield the title compound in quantitative yield.

¹H NMR (CDCl₃) δ ppm 6.43 (br s, 1H), 5.22 (d, 1H), 4.37 (q, 1H), 4.13 (q, 2H), 1.84 (m, 1H), 1.68 (sextet, 1H), 1.42 (sextet, 1H), 1.25 (t, 3H), 0.95 (t, 3H); MS (CI) 144 (100%), 190 [M+1]⁺.

d) (2R)-2-(Methylamino)pentan-1-ol

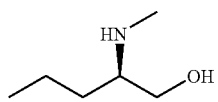

Lithium aluminium hydride (6.5 g, 171 mmol) was suspended in THF at 0° C. under a nitrogen atmosphere. N-(Ethoxycarbonyl)-D-norvaline was dissolved in THF and added dropwise at 0° C. The reaction mixture was refluxed over night. After cooling to room temperature, saturated aqueous sodium sulphate was added to form a slurry. The resulting mixture was filtered through celite. The solid was washed with DCM until all product had been extracted. The combined filtrate was dried over sodium sulphate and concentrated in vacuo. Bulb-to-bulb destillation at 0.1 mbar collecting the fraction between 75-85° C. yielded 7.1 g (71% yield) of the title compound.

¹H NMR (CDCl₃) 3.63 (dd, 1H); 3.30 (dd, 1H); 2.51 (m, 1H); 2.41 (s, 3H); 2.09 (br s, 2H); 1.50-1.28 (m, 4H); 0.93 (t, 3H); MS (CI) 86 (100%), 118 [M+1]⁺.

e) (2R)-2-{[2-Amino-5-(benzylthio)[1,3]thiazolo[4,5-d]pyrimidin-7-yl](methyl)amino}pentan-1-ol

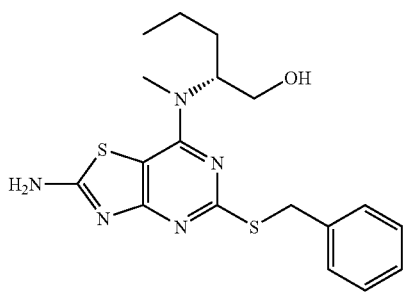

5-(Benzylthio)-7-chloro[1,3]thiazolo[4,5-d]pyrimidin-2-amine (6.0 g, 19.4 mmol) was dissolved in NMP (25 mL). DIPEA (6.8 mL, 38.8 mmol) and (2R)-2-(methylamino)pentan-1-ol (3.4 g, 29.1 mmol) were added and the mixture was heated to 120° C. for 3 days. Additional (2R)-2-(methylamino)pentan-1-ol (350 mg, 2.99 mmol) and DIPEA (1 mL, 5.74 mmol) was added and the reaction mixture was heated for 6 h at 120° C. After cooling to room temperature, the mixture was poured into ice. The precipitated product was collected by filtration and purified by flash column chromatography (eluent DCM:ethyl acetate gradient) to yield the title compound (5.74 g, 76% yield).

¹H NMR (DMSO-d₆) 7.98 (br s, 2H), 7.41 (m, 2H), 7.29 (m, 2H), 7.22 (m, 1H), 4.73 (t, 1H), 4.54 (br s, 2H), 4.33 (m, 2H), 3.55-3.40 (m, 2H), 3.01 (s, 3H), 1.52-1.44 (m, 2H), 1.25-1.10 (m, 2H), 0.84 (t, 3H); MS (ESI) m/z 390 L+1]⁺.

f) (2R)-2-[(2-Amino-5-mercapto[1,3]thiazolo[4,5-d]pyrimidin-7-yl)(methyl)amino]pentan-1-ol

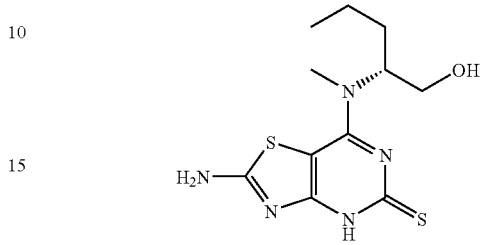

A round-bottomed flask was equipped with a dry ice-ethanol condenser and immersed in a dry ice-ethanol cooling bath. Ammonia (200 mL) was condensed into the flask followed by the addition of (2R)-2-{[2-amino-5-(benzylthio)[1,3]thiazolo[4,5-d]pyrimidin-7-yl](methyl)amino}pentan-1-ol (5.43 g, 13.9 mmol). The resulting mixture was allowed to warm to −33° C. and sodium metal was added in small pieces until a blue colour appeared and persisted for 30 seconds. The reaction was then quenched by addition of a spoon of solid ammonium chloride. The ammonia was evaporated off and water (250 mL) was added to the residue. The resulting mixture was neutralized with 1M hydrochloric acid (aq.). The precipitated product was collected by filtration, washed with water and acetonitrile and dried in vacuo to yield 3.38 g (81% yield) of the title compound.

¹H NMR (DMSO-d₆) 12.81 (br s, 1H); 8.45 (br s, 2H), 4.84 (br s, 1H), 3.55-3.40 (m, 2H), 3.02 (s, 3H), 1.48 (m, 2H), 1.21 (m, 2H), 0.87 (t, 3H); MS (ESI) m/z 300 [M+1]⁺.

g) (2R)-2-[(2-Amino-5-{[(1S)-1-(6-chloropyridin-3-yl)ethyl]thio}[1,3]thiazolo[4,5-d]pyrimidin-7-yl)(methyl)amino]pentan-1-ol

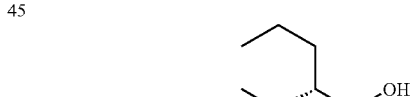

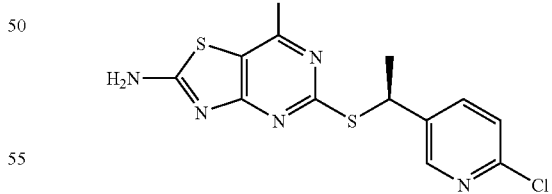

The title compound was prepared using General method A starting from (2R)-2-[(2-amino-5-mercapto[1,3]thiazolo[4,5-d]pyrimidin-7-yl)(methyl)amino]pentan-1-ol (96 mg, 0.32 mmol) and 2-chloro-5-[(1R)-1-chloroethyl]pyridine (85 mg, 0.48 mmol). Purification by flash column chromatography (eluent DCM:ethyl acetate) yielded 22 mg (16% yield) of the title compound.

¹H NMR (400 MHz, DMSO-d₆) δ ppm 8.51 (d, 1H), 7.99 (br s, 2H), 7.96 (dd, 1H), 7.45 (d, 1H); 4.98 (q, 1H); 4.73 (t, 1H); 4.46 (br s, 1H); 3.53-3.38 (m, 2H), 2.97 (s, 3H), 1.66 (d, 3H), 1.48 (m, 2H), 1.17 (m, 2H), 0.84 (t, 31); MS (ESI) m/z 439 and 441 [M+1]⁺.

EXAMPLE 7

(2R)-2-[(2-Amino-5-{[(1S)-1-(6-chloropyridin-3-yl)ethyl]thio}[1,3]thiazolo[4,5-d]pyrimidin-7-yl)amino]pentan-1-ol a) (2R)-2-{[2-Amino-5-(benzylthio)[1,3]thiazolo[4,5-d]pyrimidin-7-yl]amino}pentan-1-ol

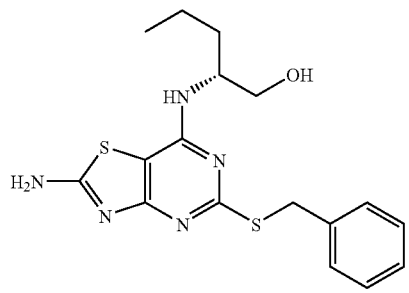

5-(Benzylthio)-7-chloro[1,3]thiazolo[4,5-d]pyrimidin-2-amine (6.0 g, 19.4 mmol) was dissolved in NMP (30 mL). DIPEA (8.4 mL, 48.5 mmol) and 2-amino-(2R)-1-pentanol (3.5 g, 33.9 mmol) were added and the mixture was heated to 110° C. for 4 days. After cooling to room temperature, the mixture was poured into water (200 mL). The precipitated product was collected by filtration, washed with water and used in the next step without further purification (7.0 g, 97% yield).
MS (ESI) m/z 376 [M+1]⁺.

b) (2R)-2-[(2-Amino-5-mercapto[1,3]thiazolo[4,5-d]pyrimidin-7-yl)amino]pentan-]-ol

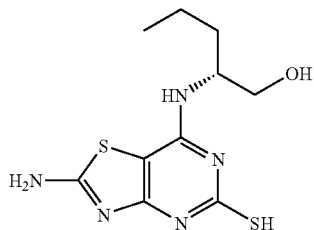

A round-bottomed flask was equipped with a dry ice-ethanol condenser and immersed in a dry ice-ethanol cooling bath. Ammonia (250 mL) was condensed into the flask followed by the addition of (2R)-2-{[2-amino-5-(benzylthio)[1,3]thiazolo[4,5-d]pyrimidin-7-yl]amino}pentan-1-ol (6.8 g, 18.1 mmol). The resulting mixture was allowed to warm to −33° C. and sodium metal was added in small pieces until a blue colour appeared and persisted for 30 seconds. The reaction was then quenched by addition of a spoon of solid ammonium chloride. The ammonia was evaporated off and water (250 mL) was added to the residue. The resulting mixture was neutralized with 1M hydrochloric acid (aq.). The precipitated product was collected by filtration, washed with water and dried in vacuo to yield 4.15 g (80% yield) of the title compound.
MS (ESI) m/z 286 [M+1]⁺.

c) (2R)-2-[(2-Amino-5-{[(1S)-1-(6-chloropyridin-3-yl)ethyl]thio}[1,3]thiazolo[4,5-d]pyrimidin-7-yl)amino]pentan-1-ol

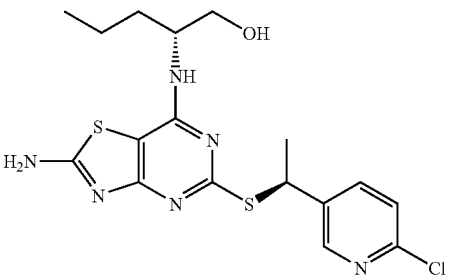

The title compound was prepared using General Method A starting from (2R)-2-[(2-amino-5-mercapto[1,3]thiazolo[4,5-d]pyrimidin-7-yl)amino]pentan-1-ol (70 mg, 0.245 mmol) and 2-chloro-5-[(1R)-1-chloroethyl]pyridine (Example 6b, 52 mg, 0.29 mmol). Purification by preparative HPLC yielded 23 mg (22% yield) of the title compound.
¹H NMR (400 MHz, DMSO-d₆) 8.50 (d, 1H); 7.99 (br s, 2H); 7.95 (dd, 1H); 7.44 (d, 1H); 6.91 (d, 1H); 4.95 (q, 1H); 4.11 (m, 1H); 3.41 (dd, 1H); 3.31 (dd, 1H); 1.64 (d, 3H); 1.56 (m, 1H); 1.41 (m, 1H); 1.4-1.2 (m, 2H); 0.85 (t, 3H); MS (ESI) m/z 425 and 427 [M+1]⁺.

EXAMPLE 8

2-{(1S)-1-[(2-Amino-7-{[(1R)-1-(hydroxymethyl)-3-methylbutyl]amino}[1,3]thiazolo[4,5-d]pyrimidin-5-yl)thio]ethyl}isonicotinonitrile

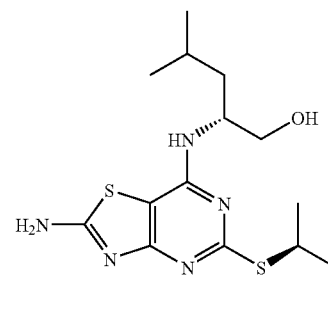

a) 2-((S)-1-Hydroxy-ethyl)-isonicotinonitrile

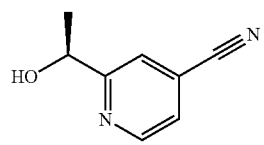

The title compound was prepared according to General Method B starting from 2-acetyl-isonicotinonitrile (2.00 g, 13.7 mmol) and (−)-DIPCl (6.58 g, 20.53 mmol) to yield the title compound (625 mg, 4.22 mmol) with 90% ee.

hu 1H NMR (CDCl$_3$) δ 8.72 (d, 1H), 7.62 (s, 1H), 7.44 (dd, 1H), 4.96 (q, 1H), 1.54 (d, 3H).

b) 2-((R)-1-Chloro-ethyl)-isonicotinonitrile

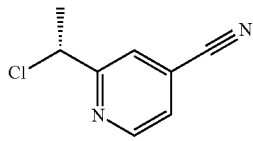

The title compound was prepared from 2-((S)-1-hydroxy-ethyl)-isonicotinonitrile (620 mg, 4.18 mmol) according to General Method C, except that 1.0 equiv. NCS and 1.0 equiv. PPh$_3$ were used. After 24 hrs reaction time another 0.2 equiv. each of NCS and PPh$_3$ were added and the temperature was increased to 30° C. for 12 h. Workup and purification by flash column chromatography yielded the title compound (46 mg, 7% yield) with 82% ee. $^1$H NMR (CDCl$_3$) δ 8.74 (d, 1H), 7.76 (s, 1H), 7.46 (dd, 1H), 5.16 (q, 1H), 1.88 (d, 3H).

c) 2-{(1S)-1-[(2-Amino-7-{[(1R)-1-(hydroxymethyl)-3-methylbutyl]amino}[1,3]thiazolo[4,5-d]pyrimidin-5-yl)thio]ethyl}isonicotinonitrile

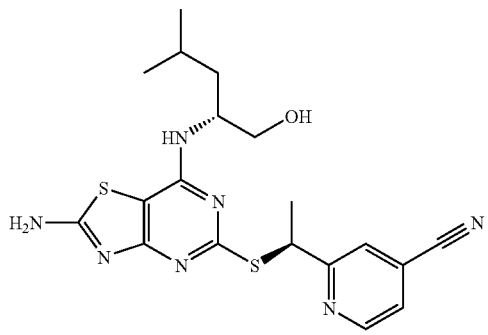

The title compound was prepared according to General Method A starting from 2-((R)-1-chloro-ethyl)-isonicotinonitrile (46 mg, 0.28 mmol) and (2R)-2-[(2-amino-5-mercapto[1,3]thiazolo[4,5-d]pyrimidin-7-yl)amino]-4-methylpentan-1-ol (69 mg, 0.23 mmol). Purification by chiral HPLC (Column: Chiralpak AD 50×150 mm, eluent: heptane:isopropanol 85:15), flowrate 60 ml/min) yielded the title compound (20 mg, 20% yield).

$^1$H NMR (400 MHz, DMSO-d$_6$) δ ppm 8.78 (d, 1 H) 8.00 (s, 1 H) 7.95 (s, 1 H) 7.72 (m, 1 H) 6.90 (m, 1 H) 5.14 (q, 1 H) 4.64 (t, 1 H) 4.23 (br s, 1 H) 3.23-3.41 (m, 2 H) 1.67 (d, 3 H) 1.64-1.52 (m, 1 H) 1.32-1.48 (m, 2 H) 0.87 (dd, 6 H); MS (ESI) m/z 430 [M+1]$^+$.

EXAMPLE 9

EXAMPLE 9a (2R)-2-[(2-amino-5-{[(1R)-1-(3-chloropyridin-4-yl)ethyl]thio}[1,3]thiazolo[4,5-d]pyrimidin-7-yl)amino]-4-methylpentan-1-ol and

EXAMPLE 9b (2R)-2-[(2-amino-5-{[(1S)-1-(3-chloropyridin-4-yl)ethyl]thio}[1,3]thiazolo[4,5-d]pyrimidin-7-yl)amino]-4-methylpentan-1-ol

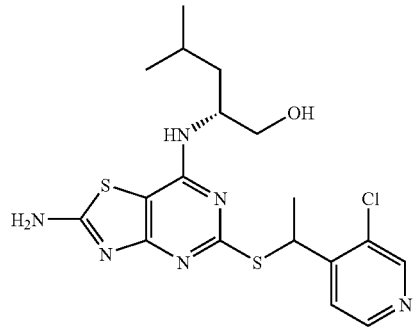

The diastereomeric mixture of (2R)-2-[(2-amino-5-{[1-(3-chloropyridin-4-yl)ethyl]thio}[1,3]thiazolo[4,5-d]pyrimidin-7-yl)amino]-4-methylpentan-1-ol (105 mg) from Example 4 was separated by preparative HPLC to yield 14 mg of the first eluting isomer (Example 9a):

$^1$H NMR (400 MHz, DMSO-d$_6$) δ ppm 8.59 (s, 1H), 8.48 (d, 1H), 8.00 (s, 2H), 7.68 (d, 1H); 6.93 (d, 1H); 5.27 (q, 1H); 4.63 (t, 1H); 4.16 (br s, 1H); 3.42-3.30 (m, 2H), 1.64 (d, 3H), 1.58-1.30 (m, 3H), 0.84 (d, 3H), 0.74 (d, 3H1); MS (ESI) m/z 439 and 441 [M+1]$^+$. and 15 mg of the last eluting isomer (Example 9b):

1H NMR (400 MHz, DMSO-d$_6$) δ ppm 8.60 (s, 1H), 8.48 (d, 1H), 8.00 (s, 2H), 7.67 (d, 1H); 6.92 (d, 1H); 5.28 (q, 1H); 4.56 (t, 1H); 4.22 (br s, 1H); 3.33-3.12 (m, 2H), 1.62 (d, 3H), 1.60-1.30 (m, 3H), 0.88 (d, 3H), 0.85 (d, 3H); MS (ESI) m/z 439 and 441 [M+1]$^+$.

Pharmacological Screens

Materials

Recombinant human fractalkine (hCX$_3$CL1) and recombinant human interleukin-8 (IL-8 or hCXCL8) were purchased from PeproTech Inc., UK. Recombinant [$^{125}$I]-fractalkine (human) and [$^{125}$I] hIL-8 with the specific activity of 2200 Ci/mmol, was purchased from NEN® Life Science Products, Inc., UK. Fluo4-AM was purchased from Molecular Probes, US. All other chemicals were of analytical grade.

Cells

The complete human CX$_3$CR1 cDNA (GenBank accession number U20350) was extracted from human brain mRNA (Superscript, Life Technologies) and ligated into pCR-Blunt II TOPO vector (InVitrogen). The insert corresponding hCX$_3$CR1 was isolated and further subcloned into pcDNA3.1zeo. Plasmid DNA was prepared using Plasmid Midi Kit (Qiagen). Using Superfect Transfection Reagent (Qiagen) according to the manufacturer's protocol the expression plasmid for hCX$_3$CR1 was then introduced into human embryonic kidney suspension (HEKS) 293 cell line containing a vector for stable expression of a chimeric G-protein G$\alpha_{qi5}$. A stable clone was generated utilizing zeocin (500 µg/mL) and hygromycin (100 µg/mL) selection. For further applications the cells were maintained in Dulbecco's modified Eagle's medium/Ham's nutrient mix F12 (DMEM/F12) containing pyridoxine and supplemented with 10% (v/v) fetal bovine serum, 2 mM L-glutamine, 100 U/ml penicillin and 100 mg/ml streptomycin, 250 µg/mL zeocin and 100 µg/mL hygromycin.

Cells expressing human CXCR2 obtained from AstraZeneca Charnwood are cultured in EMEM containing Glutamax and supplemented with 10% FBS (from PAA, Austria), 1% non-essential amino acids (NEAA), 100 U/mL penicillin and 100 µg/mL streptomycin (PEST) and 500 µg/mL geneticin/G418.

Membrane Preparation

Cells are grown at 37° C. and 5% $CO_2$ and harvested at 60-80% confluence in buffer containing 10 mM Tris-HCl pH 7.4, 5 mM EDTA, 0.1 mg/mL bacitracin. The cells are centrifuged at 300×g for 10 min and the pellet is resuspended in harvesting buffer (10 mM Tris-HCl, pH 7.4, 5 mM ethylenediaminetetra-aceticacid (EDTA) and 0.1 mg/mL bacitracin), pooled and homogenised using a Dounce homogeniser. The homogenate is centrifuged in 48000×g for 10 min and resuspended in harvesting buffer using Ultra-Turrax T8. Membrane aliquots are stored at −80° C. Protein concentration was determined in microtiter plates as described by Harrington (1990, Anal. Biochem. 186, 285-287).

In Vitro Receptor Binding Assay

Competition binding studies of [$^{125}$I]fraktalkine were performed in 2 mL 96-deep-well plates (Beckman, Germany) in a total volume of 1000 µL/well. Each well contained 10 pM [$^{125}$I]-fractalkine and membrane equivalent to receptor concentration of 1 pM in assay buffer (50 mM Hepes-KOH, pH 7.4, 10 mM MgCl$_2$, 1 mM EDTA, 0.1% (w/v) gelatine). Ten concentrations (2 points/log unit) of the test compounds were pre-dissolved in DMSO and added to reach a final concentration of 1% (v/v) DMSO. The assay was initiated with the addition of membranes and incubated at 25° C. for 24 h. The reactions were stopped by rapid filtration through Whatman GF/B glass fiber filters pretreated with 0.3% polyethylimine and subsequent washing with ice-cold buffer (10 mM Hepes-KOH pH 7.4, 500 mM NaCl) using a Brandel receptor binding harvester. Scintillation cocktail was added and radioactivity was determined in a Packard 2500TR liquid scintillation counter. (Perkin Elmer, USA)

The [$^{125}$I]-hIL-8 competition binding studies are performed in singlicates in white clear bottom 96-well isoplates with a final volume of 200 µL and each well contains 150 pM [$^{125}$I]-hIL-8 (specific activity 2200 Ci/mmol), membrane-SPA preparation equivalent to 20 pM receptors and 1.5 mg SPA-beads in assay buffer [50 mM HEPES-KOH pH 7.4, 10 mM MgCl$_2$, 1 mM EDTA, 0.5% (w/v) gelatin]. The test compounds were treated as above. The non-specific binding is determined in the presence of 500 nM unlabeled hIL-8. The agonist hIL-8 (a concentration-response curve from 3 pM to 30 nM), is used as reference compound at each test occasion. The peptide curve does not contain DMSO. The binding reaction is started by addition of 140 µL membrane-SPA preparation, and the samples are incubated in dark at RT for 4 h. Assay plates are counted in a liquid scintillation counter (Wallac MicroBeta® TriLux 1450 from PerkinElmer, USA).

[$^{35}$S]GTPγS Binding

The [$^{35}$S]GTPγS binding studies were carried out in clear-bottom microtiter plates in duplicates with 10 concentrations of the inhibitor (2 conc/log units) diluted in DMSO (final conc 1%) and at room temperature. Membranes expressing the hCX$_3$CR1 receptor (final concentration 20 µg protein/well) were added together with SPA beads (final concentration 1 mg/well) all suspended in GTPγS binding buffer (50 mM Tris-HCl, 100 mM NaCl, 0.1% gelatin, 15 µg saponin/mL and 3 µM GDP, pH 7.4 at rt). Membranes, SPA beads and drugs were pre-incubated 30 min before addition of 310 pM fraktalkine for maximal stimulation. Basal activity was defined as the activity found without fraktalkine stimulation (GTPγS binding buffer). After additional 30 min the reaction was started with the addition of [$^{35}$S]GTPγS to a final concentration of 0.1 nM and a final assay volume of 0.2 mL. The experiment was terminated 30 minutes later by centrifugation at 2000 rpm for 2×5 minutes (different directions) and the radioactivity determined in a liquid scintillation counter (Wallac MicroBeta® TriLux 1450).

Results

Typical CX$_3$CR1 Ki values for the compounds of the present invention are in the range of about 0.1 to about 1000 nM. Other values for CX$_3$CR1 Ki are in the range of about 0.1 nM to about 500 nM. Further values for CX$_3$CR1 Ki are in the range of about 0.1 nM to about 25 nM. Results from in vitro hCX$_3$CR1 binding assay for final compounds are shown in Table 1.

TABLE 1

| Example no | $K_i$ (nM) |
|---|---|
| 1 | 21 |
| 2 | 6.2 |
| 3 | 6.5 |
| 4 | Not tested* |
| 5 | 23 |
| 6 | 203 |
| 7 | 149 |
| 8 | 81 |
| 9a | Not tested |
| 9b | 35 |

*Example 4 represents the mixutre of diastereomers that are separated in Example 9.

The compounds of the present invention wherein R$^1$ represents Me (containing a branched thioalkylpyridyl group in 5-position) are both more potent antagonists at the CX$_3$CR1 receptor and/or less potent antagonists at the CXCR2 receptor than corresponding reference compounds wherein R$^1$ represents H. Such enhanced selectivity with respect to antagonism of the CX$_3$CR1 receptor is expected to result in significant therapeutic benefit.

The invention claimed is:
1. A compound of formula (I)

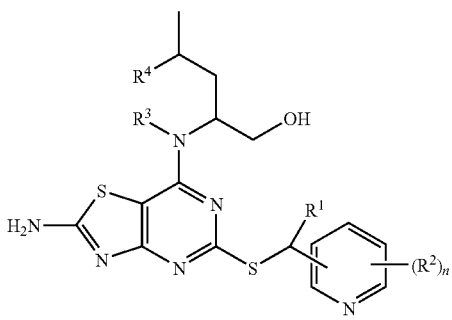

wherein:
R¹ represents CH₃ or CF₃;
R² represents halo, or CN or $C_{1-6}$alkyl;
R³ represents H or CH₃;
R⁴ represents H or CH₃;
n represents 0, 1 or 2;
as a free base or a pharmaceutically acceptable salt.

2. A compound according to claim 1, wherein n represents 1.

3. A compound according to claim 1, wherein R¹ represents CH₃.

4. A compound according to claim 1, wherein R² represents halo or CN.

5. A compound according to claim 1, wherein R² represents F or Cl.

6. A compound according to claim 1, wherein R² represents CN.

7. A compound according to claim 1, wherein n represents 1; R¹ represents CH₃; and R² represents F, Cl or CN.

8. A compound according to claim 1, wherein the pyridine is attached in its 5-position and has Cl in its 2-position.

9. A compound according to claim 1, wherein the pyridine is attached in its 2-position and has CN in its 4-position.

10. A compound according to claim 1, wherein the pyridine is attached in its 2-position and has F in its 5-position.

11. A compound according to claim 1, wherein the pyridine is attached in its 2-position and has Cl in its 5-position.

12. A compound according to claim 1, wherein the pyridine is attached in its 2-position and has F in its 3-position.

13. A compound according to claim 1, wherein the pyridine is attached in its 4-position and has Cl in its 3-position.

14. A compound according to claim 1, wherein R³ represents H.

15. A compound according to claim 1, wherein R⁴ represents CH₃.

16. A compound selected from:
(2R)-2-[(2-amino-5-{[1(5-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(5-chloropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(5-fluoropyridin-2-yl)ethyl]thio}[1,3]thiazolo[4,5-d]pyrimidin-7-yl)amino]-4-methylpentan-1-ol;
(2R)-2-[(2-amino-5-{[1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1R)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(6-chloropyridin-3-yl)ethyl]thio}[1,3]thiazolo[4,5-d]pyrimidin-7-yl)(methyl)amino]pentan-1-ol;
(2R)-2-[(2-amino-5-{[(1S)-1-(6-chloropyridin-3-yl)ethyl]thio}[1,3]thiazolo[4,5-d]pyrimidin-7-yl)amino]pentan-1-ol; and
2-{(1S)-1-[(2-amino-7-{[(1R)-1-(hydroxymethyl)-3-methylbutyl]amino}[1,3]thiazolo[4,5-d]pyrimidin-5-yl)thio]ethyl}isonicotinonitrile;
as a free base or a pharmaceutically acceptable salt.

17. A compound according to claim 1, or a pharmaceutically acceptable salt thereof, in admixture with a pharmaceutically acceptable diluent or carrier.

18. A compound according to claim 16, or a pharmaceutically acceptable salt thereof, in admixture with a pharmaceutically acceptable diluent or carrier.

* * * * *